(12) United States Patent
Lin (10) Patent No.: US 6,827,689 B2
(45) Date of Patent: Dec. 7, 2004

(54) SPHYGMORGH MEASURE METHOD AND DEVICE FOR PULSE PRESSURE AND BLOOD FLOW RATE

(75) Inventor: Chin-Yuh Lin, Taichung (TW)

(73) Assignee: E-Med Biotech Inc., Taichung (TW)

( * ) Notice: Subject to any disclaimer, the term of this patent is extended or adjusted under 35 U.S.C. 154(b) by 77 days.

(21) Appl. No.: 10/421,748

(22) Filed: Apr. 24, 2003

(65) Prior Publication Data

US 2003/0204144 A1 Oct. 30, 2003

(30) Foreign Application Priority Data

Apr. 26, 2002 (TW) ........................................ 91108622 A (51) Int. Cl.[7] .................................................. A61B 5/02
(52) U.S. Cl. ..................... 600/486; 600/485; 600/483; 600/504
(58) Field of Search ................................. 600/481, 483, 600/485, 486, 488, 500–505, 479, 480

(56) References Cited

U.S. PATENT DOCUMENTS

| | | | | |
|---|---|---|---|---|
| 4,621,646 A | * | 11/1986 | Bryant ........................ | 600/505 |
| 4,846,191 A | * | 7/1989 | Brockway et al. .......... | 600/561 |
| 6,019,735 A | * | 2/2000 | Kensey et al. ............... | 600/573 |
| 6,033,366 A | * | 3/2000 | Brockway et al. .......... | 600/486 |
| 6,354,999 B1 | * | 3/2002 | Dgany et al. ................ | 600/486 |

* cited by examiner

Primary Examiner—Max F. Hindenburg
Assistant Examiner—Navin Natnithithadha
(74) Attorney, Agent, or Firm—Rosenberg, Klein & Lee (57) ABSTRACT

A sphygmogram measure method and device, which detects pulse pressure and blood flow rate simultaneously, includes an upstream and a downstream pressure sensors provided to measure the pulse pressure of two adjacent points on radial artery. The time lag of pulse wave passing through the two pressure sensors is obtained by a time delay detection circuit. The values of pulse pressure at the upstream pressure sensor and time lag are inputted into a digital signal process unit for calculating the value of pulse pressure at the downstream pressure sensor. A thermal image device and an optical displacement sensor are used to measure the unstressed vessel's diameter and the variation of vessel's diameter. A viscometer measures the blood viscosity coefficient of blood specimen. All the values above are used to calculate vessel compliance and blood flow rate as a helpful reference of human's health status.

15 Claims, 10 Drawing Sheets

SPHYGMORGH MEASURE METHOD AND DEVICE FOR PULSE PRESSURE AND BLOOD FLOW RATE

BACKGROUND OF THE INVENTION

1. Field of the Invention

This invention relates to a sphygmorgh measure method and device for obtaining pulse pressure and blood flow rate simultaneously. More specifically, a device and a method placing two sets of sensors along the direction of bloodstream to measure the pulse pressures and the variations of vessel's diameter, then use these data to calculate dynamic compliance, blood flow rate, and hemokinetics for diagnosis on physical health status.

2. Description of Prior Art

Current methods of sphygmogram rely on measuring the pressure of the pulse and the variation of the waveform, or changing the pressure into spectrums for analysis, to evaluate the health status of a person. In addition, Doppler ultrasound to measure blood flow, and measuring the velocity of red blood cell using infrared were also used. However, these methods would only obtain single data at one time period, instead of multiple signals simultaneously. Single data of pulse pressure, blood flow, or flow rate was insufficient for expressing all aspects of cardiovascular status, because the same pulse pressure may yield different blood flow due to different diameter or compliance of vessel. Furthermore, the health status and hemokinetics are closely related that the changes cannot be accurately understood by single data of pulse pressure, flow rate or flow velocity.

Suppose that the bloodstream is a laminar flow and the vessel is a linear resilient tube, a formula of blood flow rate is as follow:

$$Q = \frac{\pi}{20\alpha L \mu}\left[\left(a_0 + \frac{\alpha P_0(t)}{2}\right)^5 - \left(a_0 + \frac{\alpha P_L(t)}{2}\right)^5\right]$$

Wherein:

Q is the blood flow rate;

$$\alpha = \frac{\Delta a}{p}$$

is the vessel compliance; $\Delta a$ is the variation of the vessel diameter; and p is the pulse pressure value;

L is the distance between two measure points;

$\mu$ the blood viscosity coefficient;

$a_0$ is the unstressed vessel diameter; and $P_O(t)$ and $P_L(t)$ are the pulse pressure values of two measure points.

Therefore, the values of the vessel compliance $\alpha$ the blood viscosity coefficient $\mu$, the vessel diameter $a_O$, the pulse pressure values of the two measure points $P_O(t)$ and $P_L(t)$, and the distance between the two measure points L are essential to calculate the blood flow rate from the above formula. Current measure methods and devices are unable to provide simultaneously all the above data in a single process by the same device.

Figure 1:
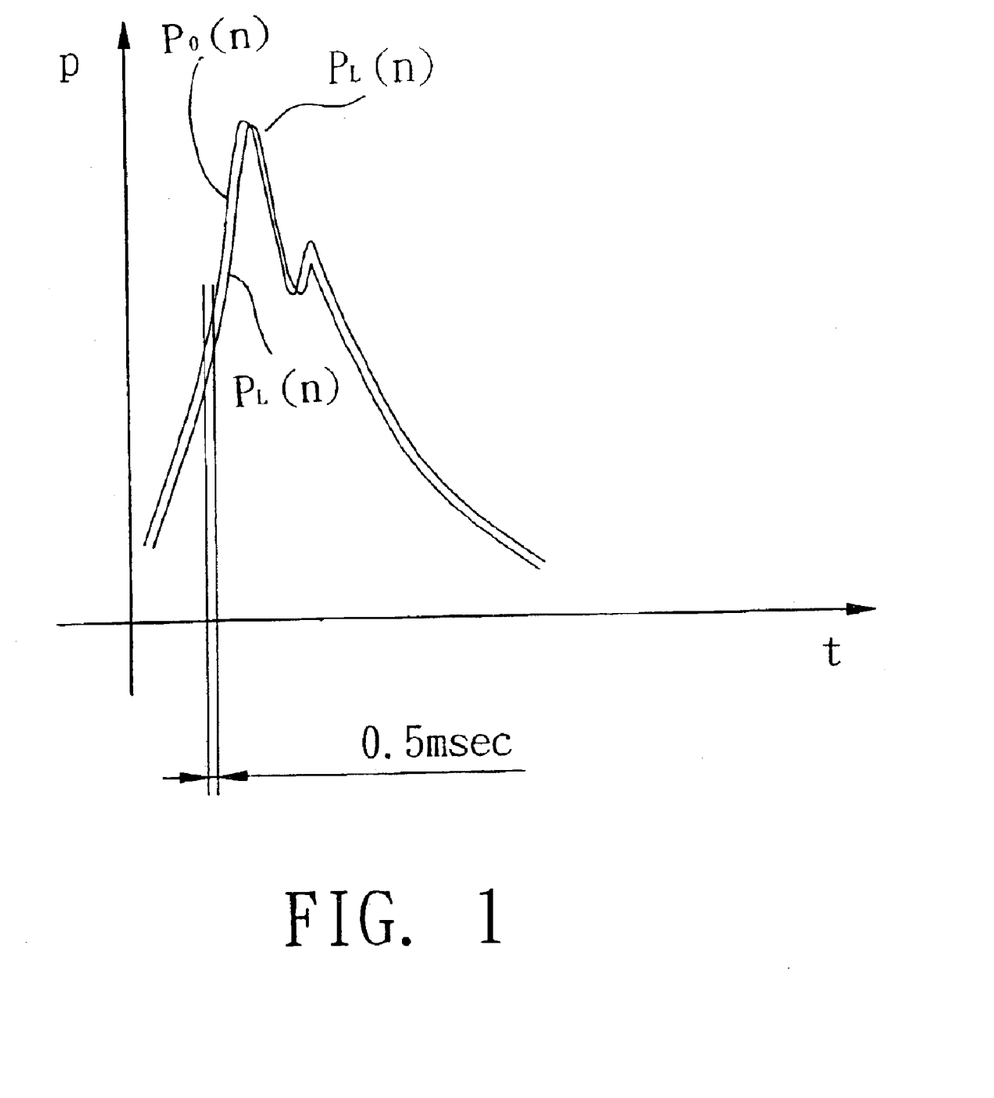
FIG. 1 is a function graph of sphygmogram that is measure by a sphygmogram measure device of the present invention.

Theoretically, to obtain the blood flow rate in accordance with above formula, the shorter the distance between two measure points is, the more accurate the estimate of blood flow rate can be. But it will be more difficult to measure pulse pressures of two measure points when the distance is closer. According to traditional Chinese medicine, the two measure points must be within one fingertip, that is, the distance between the two measure points will be appropriate between 2 to 3 mm. Refer to FIG. 1, the pulse wave velocity (PWV) in human radial artery at wrist is about 3.5 to 4.5 m/sec, which the pulse takes approximately 0.5 millisecond to pass through these two points; and most of current-in-used sphygmorgrah devices sample the pulse pressure by frequencies from 200 to 400 Hz, i.e. a period from 20 to 50 millisecond, which obviously indicates that these devices are not able to distinguish the difference of pulse pressures at these closed points.

Besides, the difference of pulse pressure between two adjacent points is rather small, it makes difficult to convert pulse pressures from analog signal into digital signal with satisfied resolutions.

Another important factor affecting the outcome of calculation for blood flow rate is vessel compliance $\alpha$. A research on carotid artery shows that practical vessel compliance is non-linear which varies during arterial systole and diastole. It means that the above formula should be modified, because the vessel compliance $\alpha$ is no longer a constant value.

Based upon the definition of the vessel compliance, the ratio of the variation of vessel's diameter to the pulse pressure, or the slope of a variation of vessel's diameter and pulse pressure curve at measure point, intuitionally, it seems simply install a pressure sensor and a displacement sensor at measure point to acquire the pulse pressure signal and the variation of vessel's diameter signal and then to calculate the nonlinear vessel compliance in a digital processing unit. But in reality, it is not applicable for noninvasive solution: at measure point, a pressure sensor should be holding stationary at certain depth against the vessel to have pressure signals; a displacement sensor should be placed to sense the variations of the vessel's diameter. A stationary pressure sensor and a movable displacement sensor cannot be connected together to have both pressure and variations of vessel's diameter at same measure point which results in failure of computing nonlinear vessel compliance.

As mentioned above, current methods and devices can acquire neither the values of two pulse pressures $P_O(t)$ and $P_L(t)$, nor the vessel compliance $\alpha$.

Accordingly, there is a need for an improved sphygmogram measure method and device, which provide solutions to the disadvantages of current counterparts.

SUMMARY OF THE INVENTION

It is therefore the objective of the present invention is to provide a sphygmogram measure method and device, which acquire pulse pressure and a blood flow rate simultaneously with the steps of:

A. Using a thermal array sensor and a thermal image identification technique to locate the artery and estimate the diameter of the vessel $a_O$;

B. Positioning an upstream pressure sensor and a downstream pressure sensor along the direction of the bloodstream to have pulse pressure $P_O(t)$ and $P_L(t)$ respectively, detecting the time lag $\tau$ between the upstream pressure and downstream pressure, sampling analog upstream pressure signal into digital form $P_O(n)$, input $P_O(n)$ and $\tau$ to a digital signal process unit, computing the digital form of downstream pressure by $P_L(n) \cong P_L(n+\tau)$;

C. There are two methods to obtain nonlinear vessel compliance as follow.

(a) For invasive approach, placing an optical displacement sensor at the downstream measure point to measure the variation of vessel's diameter, in the mean time, piercing a pressure sensor into the blood vessel to obtain the pulse pressure, entering these signals to a digital signal process unit and calculating the nonlinear vessel compliance $\alpha(n)=\Delta a(n)/P_L(n)$; and (b) For noninvasive approach, a pressure feedback control method is employed. By moving upward and downward of the downstream pressure sensor to main the pressure sensor just contact the vessel and record the movement of the pressure sensor, that is, the variation of the vessel's diameter $\Delta a(n)$, and use the term method to have $P_L(n)$, then the nonlinear vessel compliance is computed by $\alpha(n)=\Delta a(n)/P_L(n)$;

D. Entering the blood viscosity coefficient $\mu$ by using viscometer or databank;

E. Computing the blood flow rate and hemokinetic energy; and

F. Extracting the biomedical features from these data and constructing a diagnosis base databank to examine the human's health status.

Further benefits and advantages of the present invention will appear in the following descriptions and drawings.

DETAILED DESCRIPTION OF THE INVENTION

Figure 2:
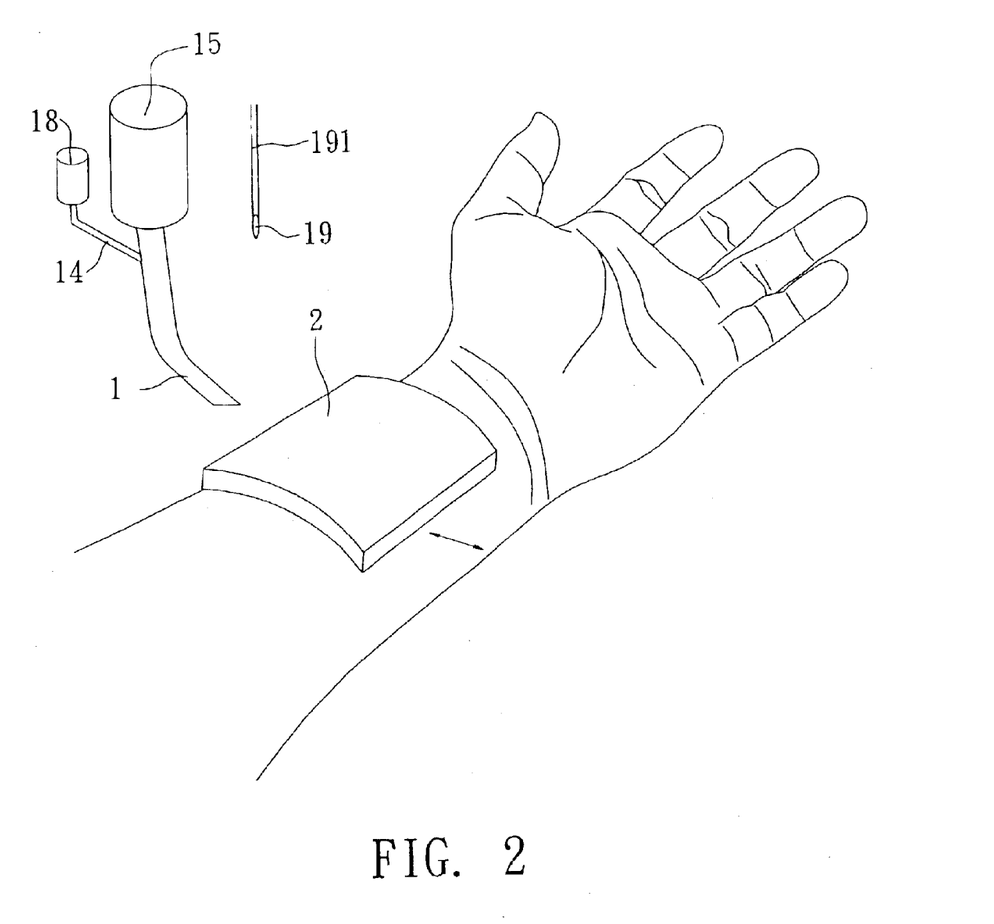
FIG. 2 is a perspective view of the sphygmogram measure device of the present invention.
Figure 3:
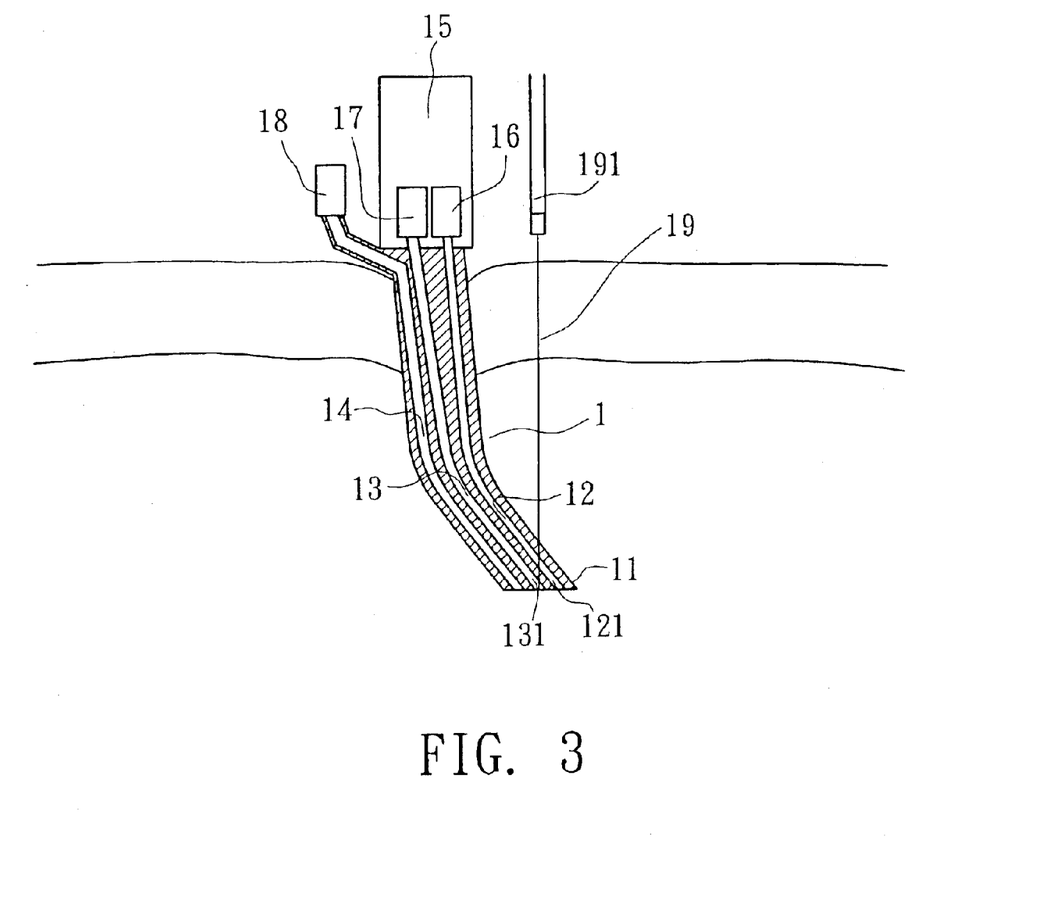
FIG. 3 is an operational side plan view in cross section of the sphygmogram measure device in FIG. 2.

The first embodiment of a sphygmogram measure device in accordance with the present invention is described in detail with reference to FIG. 2 and FIG. 3. This embodiment adopts a structure of invasive approach that comprises an intubating element (1), a probe tube (14), an optical displacement sensor (19), a thermal imaging device (2), and a digital signal process unit (not shown).

The intubating element (1) includes a sharpened end (11) that pierces through the human skin into the vessel, a first passage (12) and a second passage (13) in the intubating element. A distance between the first passage (12) and the second passage (13) is about 2 to 3 millimeters. The first passage (12) and the second passage (13) respectively communicate with a first opening (121) and a second opening (131) that are defined in the sharpened end of the intubating element (1). The second opening (131) is positioned downstream the first opening (121) in accordance with the direction of bloodstream.

The other end of intubating element (1) has a seat (15) mounted thereon. A first pressure sensor (16) and a second pressure sensor (17) are mounted in the seat (15) and sense the pressure through the first passage (12) and the second passage (13) respectively.

A probe tube (14), defined in the intubating element (1), is inserted into the vessel with one end defined in the sharpened end (11) and connected to a viscometer (18) at the other end. The viscometer (18) is provided to measure the blood viscosity coefficient $\mu$ An optical displacement sensor (19) mounts on one end of a needle (191). The needle (191) is placed above the skin of the downstream measure point near (131) to sense the variation of the vessel's diameter.

A thermal image device (2) comprises a thermal array sensor (not shown) and an image process unit (not shown) locating the vessel position and estimating the unstressed vessel's diameter. Furthermore, the thermal imaging device (2) can provide the examinee's temperature as well.

A digital signal process unit (not shown) is connected the first pressure sensor (16), the second pressure sensor (17), the viscometer (18), the optical displacement sensor (19) and the thermal image device (2). The digital signal process unit is provided to operate the required processes for gathering the various data from the sensors and calculate the pulse pressure, the vessel compliance, the blood flow rate and the hemokinetics. These values are provided a reference basis for clinical diagnosis.

The following procedures show the operating of the invasive measure device in accordance with the present invention:

A. The thermal imaging development device (2) is positioned above the vessel and estimates the unstressed diameter of the vessel.

Figure 4:
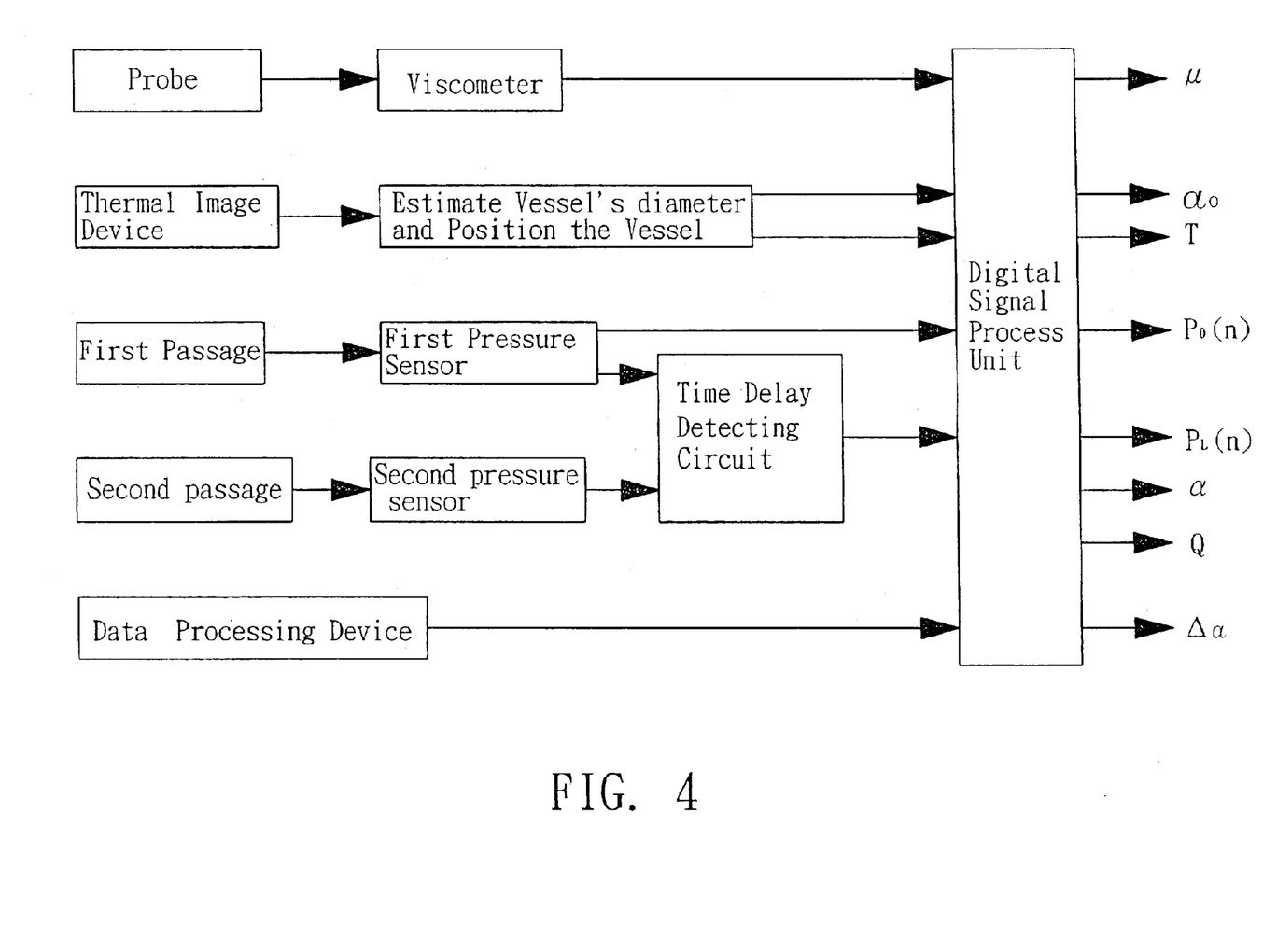
FIG. 4 is a flow chart for showing how the sphygmogram measure device of the present invention obtaining various data.

B. The intubating element (1) and the needle (191) with the optical displacement sensor (19) are inserted into the artery vessel to acquire the upstream pressure $P_O(t)$ and downstream pressure $P_L(t)$. Referring to FIG. 4, a delay time detection circuit detects the time lag $\tau$ between these two pressures. The digitized upstream pressure signal $P_O(n)$ and time lag $\tau$ are stored in the digital signal process unit. Finally, a digitized downstream pressure $P_L(n)$ is computed based upon the upstream pressure $P_O(n)$ and time lag $\tau$.

C. The variation of the vessel's diameter $\Delta a(n)$ from optical displacement sensor (19) and the downstream pressure $P_L(n)$ from the second pressure sensor (17) into digital signal process unit are acquired and provided to calculate the nonlinear vessel compliance $\alpha(n)=\Delta a(n)/P_L(n)$.

D. The blood viscosity coefficient $\mu$ is measured and read from the viscometer (18).

E. The blood flow rate Q and the hemokinetics E is computed by using the data of the blood viscosity coefficient $\mu$, the unstressed vessel's diameter $a_O$, the pulse pressures $P_O(n)$ and $P_L(n)$, and the nonlinear vessel compliance $a(n)$.

F. The features of these data and construct a databank are extracted and provided to diagnose the human's health status.

Figure 5:
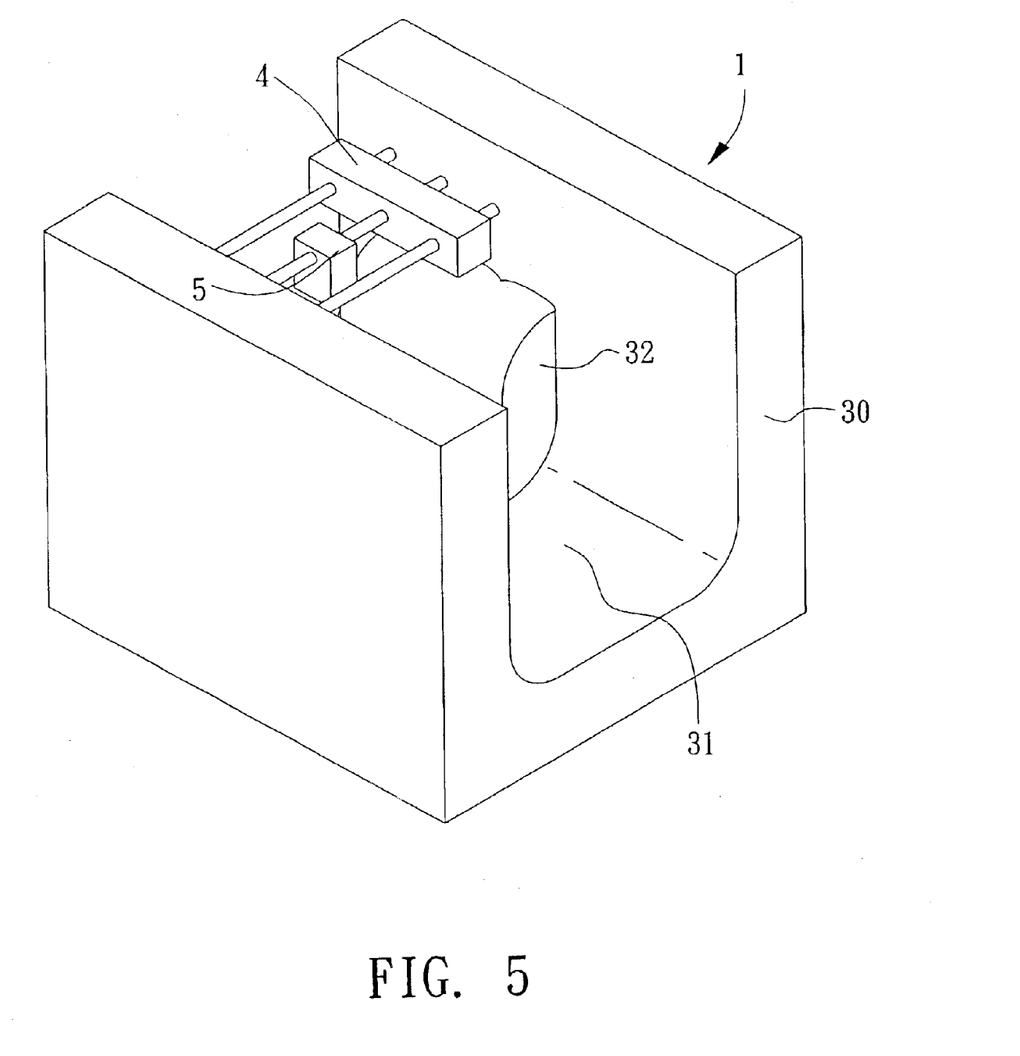
FIG. 5 is a perspective view of a second embodiment of the sphygmogram measure device of the present invention.

FIG. 5 shows the second embodiment of a noninvasive sphygmogram measure device. This embodiment comprises a wrist holder (3), a thermal image device (4), a set of pressure-sensing device (5), and a digital signal process unit (not shown).

A wrist holder (3) includes a seat (30) in which a receiving space (31) is longitudinally defined. The receiving space (31) is adapted to place an examinee's wrist with the side of radial artery therein upward. Two bladders (32) secure the wrist respectively on the two sidewalls of receiving space (31), and function to stabilize the wrist (but not press over the radial artery) when filled with air gradually.

A thermal image device (4) comprises a thermal array sensor and a thermal image process unit (not shown) mounted on the seat (30) to locate the artery vessel and estimate the unstressed vessel's diameter. At present a thermal array sensor with 128×128 pixels in a 1 cm×1 cm chip is in commercial. It can detect the temperature difference within 0.02° C. that makes the location of the radial artery in wrist and the estimation of the unstressed vessel's diameter feasible. Furthermore, the thermal image device (4) can provide the temperature information.

Figure 6:
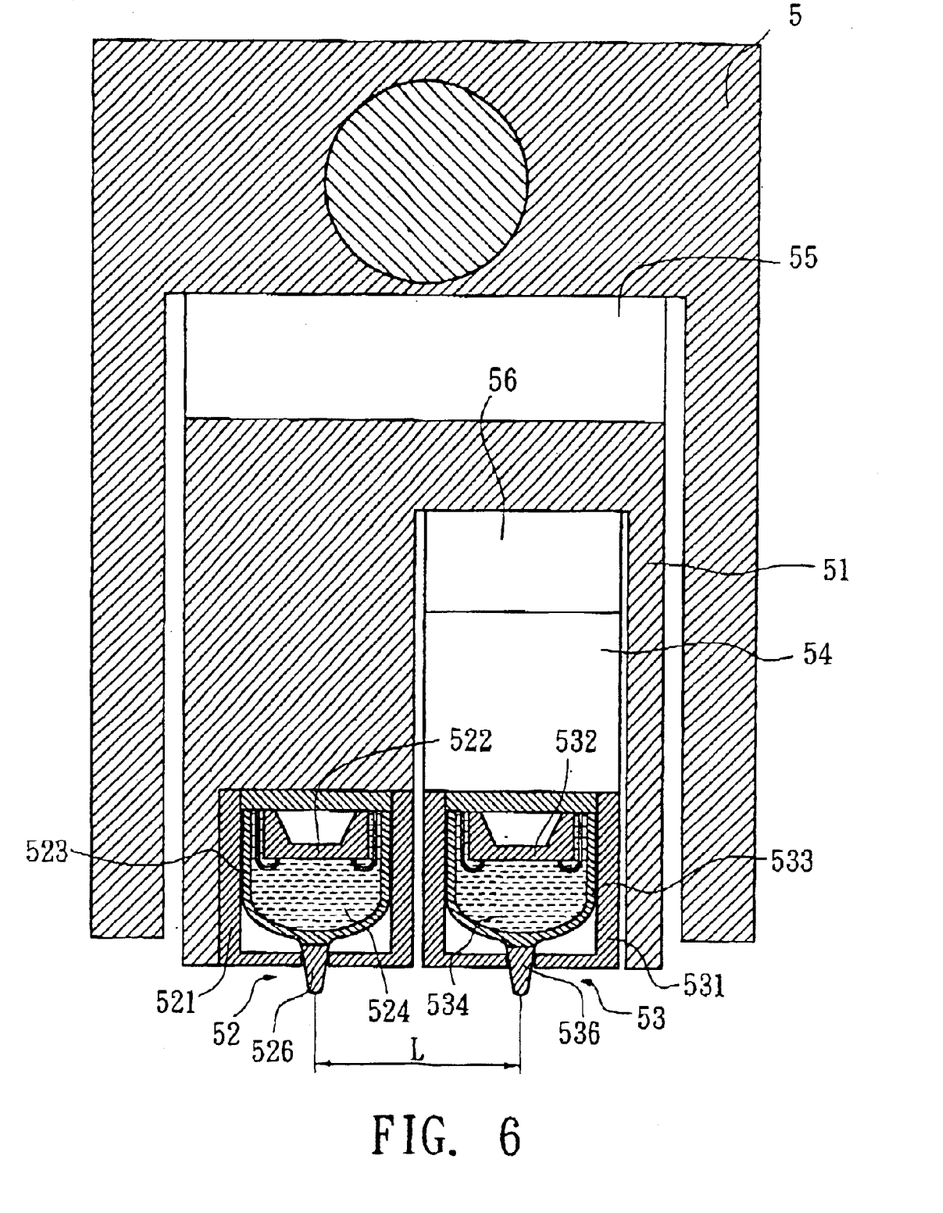
FIG. 6 is a side plan view of a pressure sensing device of the present invention in FIG. 5.
Figure 9:
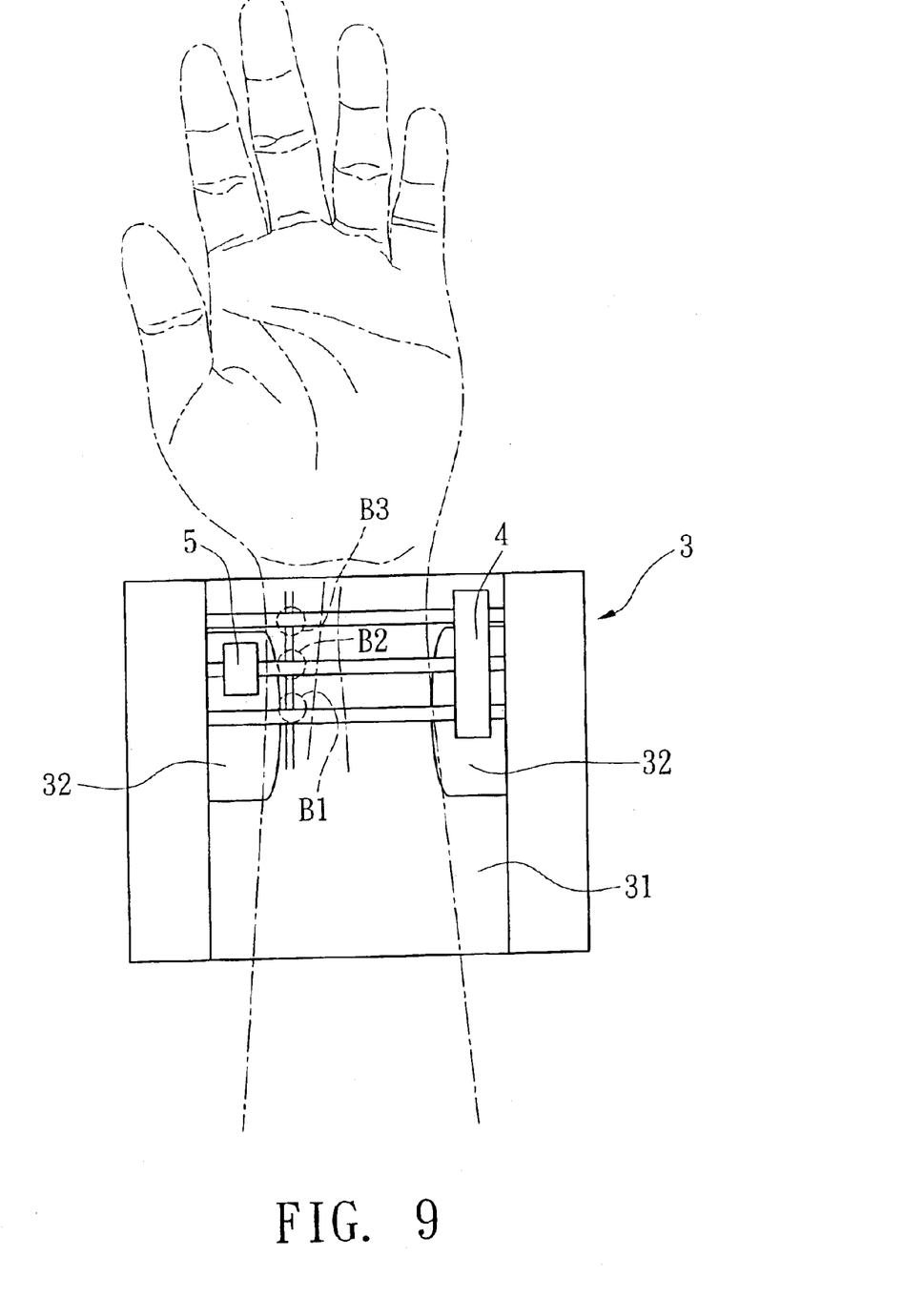
FIG. 9 is top operational plan view of the sphygmogram measure device in FIG. 5.

Reference to FIGS. 5, 6 and 9, the radial artery in the wrist has three points called Tsun (B3), Kuan (B2) and Chih (B1) respectively.

Corresponding to the point of Kuan (B2) on the wrist, a set of pressure-sensing device (5) is installed in the wrist holder (3) above the two bladders (32). The pressure-sensing device (5) includes a seat (51) that allows placing a wrist under examination, and a driving device (55) is disposed to downward press the seat (51). An upstream pressure sensor (52) and a downstream pressure sensor (53) mount respectively on the bottom side of the seat (51). The distance between the centers of upstream pressure sensor (52) and downstream pressure sensor (53) is about 2 to 3 millimeters. For a more accurately measure, a pressure sensor (52/53) is further provided to press on the point call Tsun (B3) and a pressure sensor (52/53) is further provided to press on the point called Chih (B1).

The upstream pressure sensor (52) comprises a first casing (521) mounted in the seat (51), an upstream micro-pressure sensor (522) mounted in the first casing (521) and a first resilient cover (523) covering the upstream micro-pressure sensor (522). In the same way, the downstream pressure sensor (53) includes a second casing (531) mounted in the seat (51), a downstream micro-pressure sensor (532) mounted in the second casing (531) and a second resilient cover (533) covering the downstream micro-pressure sensor (532) in pressure-sensing device (5).

A first chamber (524) is defined between the upstream micro-pressure sensor (522) and the first resilient cover (523) and fills with silicon oil, and a second chamber (534) is defined between the downstream micro-pressure sensor (532) and the second resilient cover (533) and filled with silicon oil for transmitting pressure. A first column head (526) on the central top of the first resilient cover (523) extends out of the bottom edge of the first casing (521) about 0.25 mm, and a second column head (536) on the tip of the second resilient cover (533) stand out the bottom edge of the second casing (531). The first and second column heads (526, 536) are made of hard material that can endure pressure and prevent the column head from deformity. When the pulse presses the column heads (526, 536), then transmits through the silicon oil in the first and second chambers (524, 534) to the upstream micro-pressure sensor (522) and the downstream micro-pressure sensor (532) respectively.

A first actuator (54) is mounted in the seat (51) and drives the downstream pressure sensor (53) downward and upward to obtain the variation of the vessel's diameter. In this preference embodiment of the present invention, the first actuator (54) may be a piezoelectric actuator, a shape-memory-alloy actuator or a micro actuator. An optical displacement sensor (56) is mounted on the first actuator (54) and records the variation of the vessel's diameter $\Delta a(n)$.

A digital signal process unit processes a variety of signals and data from the hardware circuit system for calculating the pulse pressure, vessel compliance, blood flow rate, and hemokinetic energy. Then extracting the biomedical features from these data and constructing a databank will be useful for diagnosis of human's health status or reexamination of traditional Chinese medicine.

Figure 7:
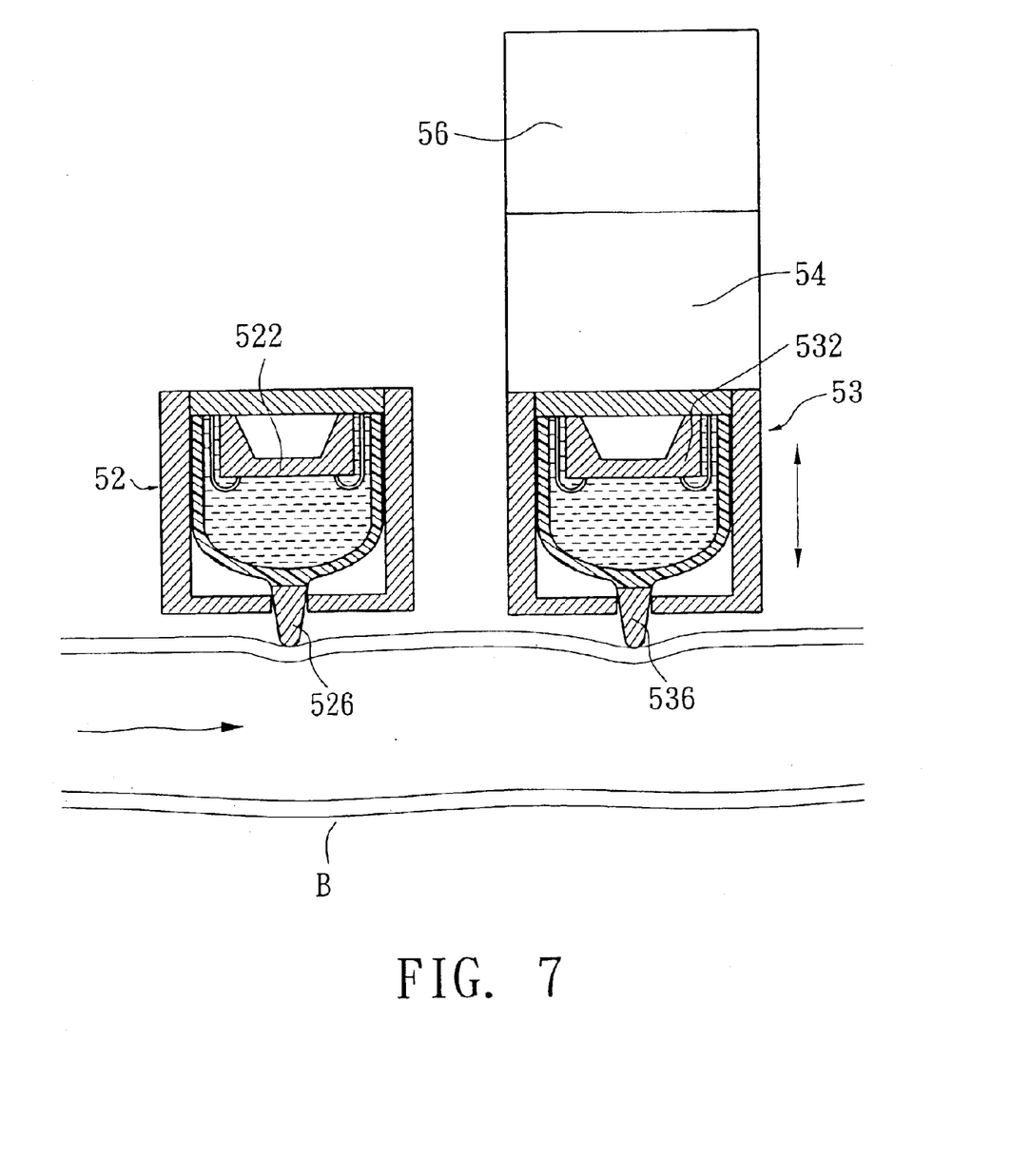
FIG. 7 is a partially side plan view of a pressure sensing device of the present invention in FIG. 5.
Figure 8:
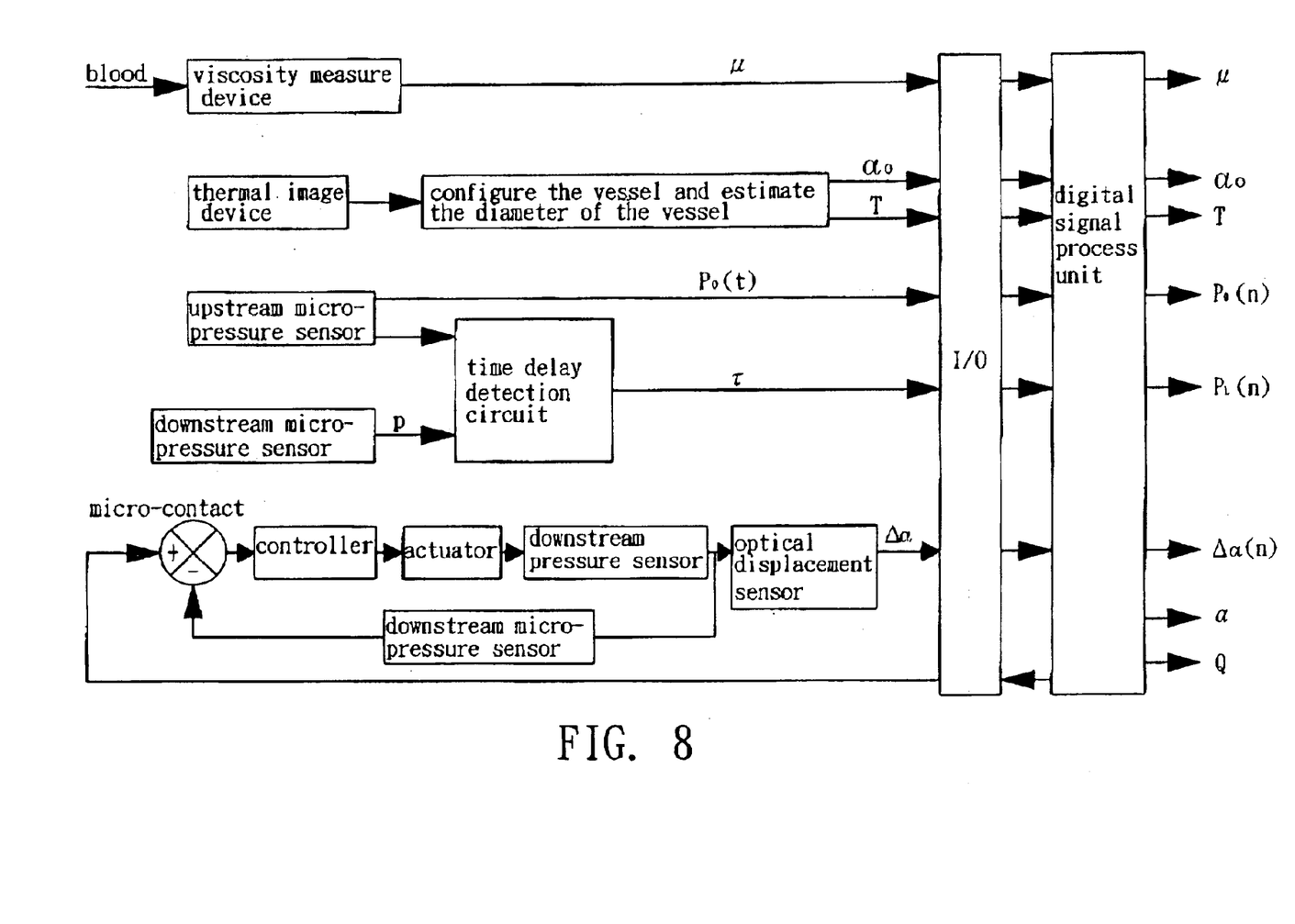
FIG. 8 is a diagram of a second embodiment of the sphygmogram measure device in FIG. 5.

FIG. 6 and FIG. 7 show the implementation of the preference embodiment on measuring the pulse pressure of two adjacent points. The driving device (55) pushes down the upstream pressure sensor (52) and the downstream pressure sensor (53) against radial artery in the wrist. The first column head (526) and the second column head (536) transmit the pulse pressure from the corresponding measure points to the upstream micro-pressure sensor (522) and the downstream micro-pressure sensor (532) respectively. Referring to FIG. 8, a time delay detection circuit detects the time lag $\tau$ between two adjacent pressures, and store the digitized upstream pressure signal $P_O(n)$ and the time lag $\tau$ in digital signal process unit, and then computes a digitized downstream pressure $P_L(n) \cong P_O(n+\tau)$ To obtain the nonlinear vessel compliance $\alpha(n)$, a pressure feedback control approach is used. The first actuator (54) moves the downstream pressure sensor (53) up and down to control the downstream pressure near zero, and the optical displacement sensor (56) connected with the first actuator (54) records the variation of vessel's diameter $\Delta a(n)$. The corresponding downstream pressure $P_L(n)$ will be calculated by the method shown in previous paragraph. The digital signal process unit then computes the nonlinear vessel compliance by $\delta(n) = \Delta(n)/P_L(n)$.

FIG. 8 and FIG. 9 describe the functions of the noninvasive sphygmogram measure device of the present invention. The operation procedure is depicted as follow.

A. An examinee's wrist with the side of radial artery therein upward is placed in the wrist holder (3).

B. The thermal image device (4) is positioned above the vessel and estimates the unstressed diameter of the vessel and the position of the radial artery.

C. The column heads (526, 536) are downward moved against the vessel to acquire the upstream pressure $P_O(t)$ and downstream pressure $P_L(t)$. Referring to FIG. 8, a time delay detection circuit detects the time lag $\tau$ between the two pressures. The digitized upstream pressure signal $P_O(n)$ and time lag $\tau$ are stored in digital signal process unit that computes a digitized downstream pressure $P_L(n)$.

D. Performing the pressure feedback control approach to obtain the variation of the vessel's diameter $\Delta a(n)$ from optical displacement sensor (56), and operating the term to obtain the downstream pressure $P_L(n)$, then calculating the nonlinear vessel compliance $\alpha(n) = \Delta a(n)/P_L(n)$ in the digital signal process unit.

E. Measuring the blood viscosity coefficient pt from the viscometer (18).

F. Computing the blood flow rate Q and the hemokinetics by using the data of the blood viscosity coefficient $\mu$, the unstressed vessel's diameter $a_O$, the pulse pressures $P_O(n)$ and $P_L(n)$ and the nonlinear vessel compliance $\alpha(n)$.

G. Extracting the features of these data and constructing a databank to diagnose the human's health status.

In order to mimic the pulse palpation at measure points of Tsun (B1), Kuan (B2) and Chih (B3) in traditional Chinese medicine, two extra pressure sensors mount on the points of Tsun (B1) and Chih (B3). Each pressure sensor contains a micro-pressure sensor and presses against Tsun (B1) or Chih (B3) after driven downward by an actuator device to measure the pulse pressure of the corresponding point in radial artery. Besides, there are three options of depth corresponding to the pressing forces (Fu, Chung, and Chen) at measure points of Tsun (B1), Kuan (B2) and Chih (B3) to improve the accuracy of the diagnosis.

Figure 10:
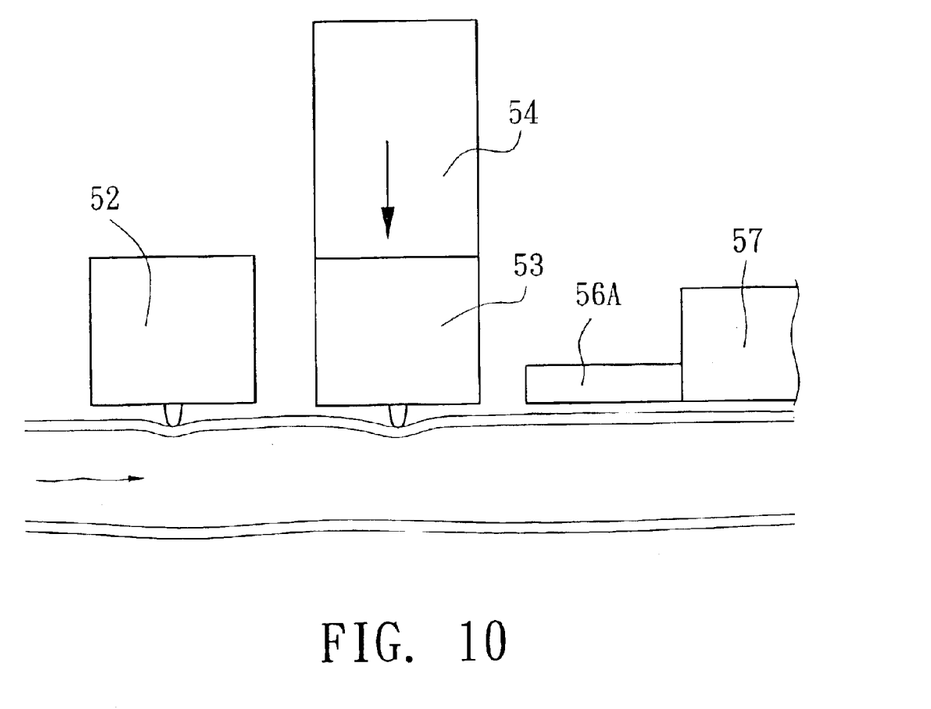
FIG. 10 is side operational plan view of a third embodiment of a sphygmogram measure device of the present invention.
Figure 11:
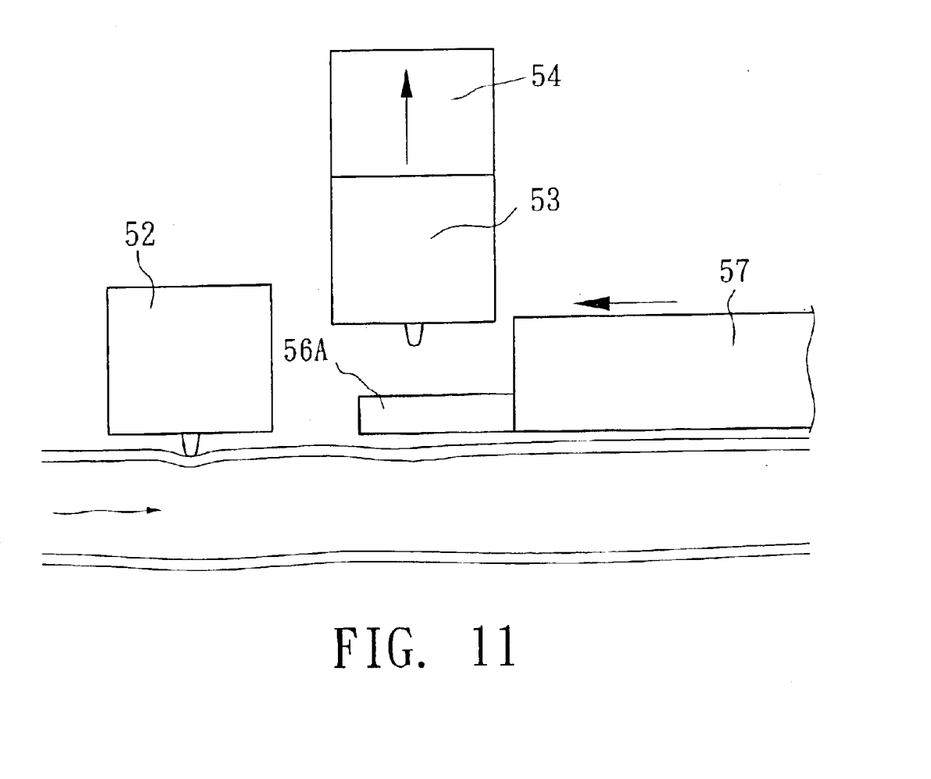
FIG. 11 is side operational plan view of the third embodiment of a sphygmogram measure device of the present invention.

With reference to FIG. 10 and FIG. 11, the third embodiment of the present invention is mostly similar to the second embodiment shown in FIG. 6, but is characterized by the downstream pressure sensor (53) without a displacement device. An optical displacement device (56A) is mounted on a second actuator device (57). Once the measurement of $P_O(n)$ and $\tau$ is completed and the downstream pressure sensor (53) is raised, the optical displacement device (56A) is moved to the position under the downstream sensor (53) and measures directly the variation of vessel diameter $\Delta a(n)$, which is then sent with the value of upstream pressure $P_O(n)$ to the digital signal process unit. Then the value of downstream pulse pressure $P_L(n)$ is calculated by using the values of $P_O(n)$ and time lag $\tau$, and the vessel compliance is ratio of the variation of vessel diameter $\Delta a(n)$ and the value of downstream pulse pressure $P_L(n)$.

While the invention has been described by means of preferred embodiments, numerous possible modifications and variations could be made thereto by those skilled in the art without departing from the scope of the inevention set forth in the claims.

What is claimed is:

1. A sphygmogram measure method for simultaneously acquiring the information of pulse pressure and blood flow rate, comprising the following steps:
    step 1: using a upstream pressure sensor and a downstream pressure sensor arranged at a certain distance L in accordance with the bloodstream direction to measure pulse pressures of $P_O(t)$ and $P_L(t)$ of two adjacent points on radial artery respectively;
    step 2: using a time delay detecting circuit to determine time lag $\tau$ related to the passage time of a pulse wave passing from the upstream pressure sensor to the downstream pressure sensor;
    step 3: inputting pulse pressure $P_O(t)$ at the upstream pressure sensor and time lag $\tau$ into a digital signal process unit which takes the values of pulse pressure $P_O(n)$ and time lag $\tau$ to calculate the value of pulse pressure $P_L(n)$ at the downstream pressure sensor;
    step 4: using an optical displacement sensor to sense the variation of vessel diameter $\Delta a(n)$ at the downstream pressure sensor;
    step 5: calculating the nonlinear vessel compliance in a digital signal process unit, $\alpha(n)=\Delta a(n)/P_L(n)$;
    step 6: using a thermal image device to estimate the unstressed vessel's diameter $a_O$ at the downstream pressure sensor;
    step 7: using a viscometer to acquire the blood viscosity coefficient $\mu$; and
    step 8: taking the above values $P_O(n)$, $P_L(n)$, L, $a_O$, $a(n)$ and $\mu$ to calculate the blood flow rate and other information.

2. The sphygmogram measure method as claimed in claim 1, wherein the distance between the upstream pressure sensor and the downstream pressure sensor is 2 to 3 millimeters.

3. The sphygmogram measure method as claimed in claim 1, wherein the upstream pressure sensor and the downstream pressure sensor access to the pulse pressure of an examinee's radial artery by an invasive method, wherein an intubating element is inserted into the vessel.

4. The sphygmogram measure method as claimed in claim 1, wherein the upstream pressure sensor and the downstream pressure sensor access to the pulse pressure of radial artery by a non-invasive method, wherein the pressure sensors contact the skin region corresponding to the measure points at the vessel.

5. The sphygmogram measure method as claimed in claim 4, wherein the upstream pressure sensor and the downstream pressure sensor pressing upon the skin tissue over radial artery are set in three depths corresponding to the pressing forces for pulse palpation in traditional Chinese medicine.

6. The sphygmogram measure method as claimed in claim 4 further comprising an actuator device driving the downstream pressure sensor downwardly and upwardly to control the downstream pressure value being very close to zero, and the movement of the downstream pressure sensor being measured by an optical displacement sensor and read as the variation of the vessel diameter.

7. The sphygmogram measure method as claimed in claim 6, wherein the optical displacement sensor is moved under the downstream pressure sensor and directly measures the variation of the vessel diameter.

8. The sphygmogram measure method as claimed in claim 4, wherein the upstream pressure sensor and the downstream pressure sensor press on a point called Kuan.

9. The sphygmogram measure method as claimed in claim 8 further comprising a pressure sensor pressing on a point called Tsun and a pressure sensor press on a point called Chih.

10. A sphygmogram measure device for a pulse pressure and a blood flow rate comprising:
    an intubating element including:
        a sharpened end pierced through the human skin and into the vessel of the human body;
        a first passage and a second passage defined in the intubating element, a distance between the first passage and the second passage being between 2 to 3 millimeters;
        a first opening defined in the sharpened end of the intubating element and communicating with the first passage;
        a second opening defined in the sharp end of the intubating element and communicating with the second passage, the second opening situated on the downstream of the blood flow related to the first opening;
        a seat mounted on the intubating element opposite to the sharp end;
        a first pressure sensor mounted in the seat and connected to the first passage for sensing the pressure in the first passage; and
        a second pressure sensor mounted in the seat and connected to the second passage for sensing the pressure in the second passage;
    a probe defined in the intubating element for sampling and measuring the blood viscosity coefficient;
    a vessel diameter measure device for measuring the diameter of the vessel; and
    an optical displacement sensor mounted on one end of the needle above the radial artery and corresponds to the second opening of the second passage for measuring the variation of the vessel diameter near the second opening of the second passage.

11. The sphygmogram measure device as claimed in claim 10, wherein the optical displacement sensor is mounted on a second actuator that drives by the optical displacement sensor.

12. The sphygmogram measure device as claimed in claim 10, wherein the vessel diameter measure device is a thermal image device, and includes a thermal array sensor and an image process unit adapted to locate the radial artery in the wrist and estimate the vessel's diameter.

13. The sphygmogram measure device as claimed in claim 11, wherein the vessel diameter measure device is a thermal image device, and includes a thermal array sensor and an image process unit adapted to locate the radial artery in the wrist and estimate the vessel's diameter.

14. The sphygmogram measure device as claimed in claim 12, wherein the thermal image device is further used to measure the body temperature.

15. The sphygmogram measure device as claimed in claim 13, wherein the thermal image device is further used to measure the body temperature.

* * * * *